United States Patent [19]

Davies et al.

[11] Patent Number: 5,055,462
[45] Date of Patent: Oct. 8, 1991

[54] CEPHALOSPORIN COMPOUNDS

[75] Inventors: Gareth M. Davies, Macclesfield; Colin J. Strawson, Congleton, both of England; Jean J. Lohmann, Hermonville, France

[73] Assignees: Imperial Chemical Industries plc, London, England; ICI Pharma, Cergy Cedex, France

[21] Appl. No.: 349,662

[22] Filed: May 10, 1989

[30] Foreign Application Priority Data

May 10, 1988 [GB] United Kingdom ............... 8811055

[51] Int. Cl.$^5$ ............... C07D 501/38; A61K 31/545
[52] U.S. Cl. ............................... 514/202; 514/201; 514/206; 540/221; 540/222; 540/225
[58] Field of Search .................. 514/201, 202, 206; 540/222, 221, 225

[56] References Cited

U.S. PATENT DOCUMENTS 4,855,420 8/1989 Jung ............................... 540/222

FOREIGN PATENT DOCUMENTS 0267733 5/1988 European Pat. Off. .

Primary Examiner—Nicholas S. Rizzo
Attorney, Agent, or Firm—Cushman, Darby & Cushman

[57] ABSTRACT

Cephalosporin antibiotics having a 3-position substituent of the formula:

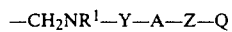

are described, wherein $R^1$ is hydrogen or certain optionally substituted alkyl groups; Y is —CO— or —SO$_2$—; A is optionally substituted phenylene or heterocyclylene; Z is a linking group and Q is a catechol or related ring system. Processes for their preparation and use are described.

6 Claims, No Drawings

CEPHALOSPORIN COMPOUNDS

The present invention relates to cephalosporins and in particular to such compounds comprising an amide or sulphonamide group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans. The compounds of this invention also have non-therapeutic uses as they can be used in conventional manner in industry for example they can be used as disinfectants and food preservatives. The compounds of this invention, however, are primarily of therapeutic interest as they show a desirable profile of activity in their antibacterial effect.

Investigation into new cephalosporin derivatives has been intense over the past 25 years with many thousands of patents and scientific papers having been published. A particular problem associated with the commercially available cephalosporins is the lack of potency against strains of Pseudomonas. The present invention provides cephalosporin derivatives having novel 3-position substituents, which derivatives possess good antibacterial activity and in particular against strains of Pseudomonas.

A further problem associated with many commercially available cephalosporins is the lack of stability to β-lactamase enzyme producing organisms and the consequent loss of antibacterial activity. The compounds of the present invention exhibit good stability to β-lactamase enzymes and thus are particularly useful in treating organisms that are β-lactamase producers.

The cephalosporin derivatives referred to herein are generally named in accordance with the 'cephem' nomenclature and numbering system proposed in J.A.C.S. 1962, 84,3400 and as depicted hereinbelow:

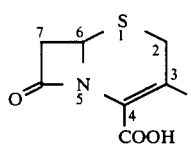

Accordingly the present invention provides a cephalosporin compound having a 3-position substituent of the formula (I):

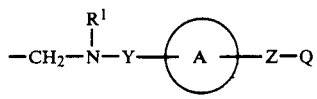

wherein Q is:

i) a benzene ring (optionally fused to a further benzene ring so forming a naphthyl group or optionally fused to a 5 or 6 membered heterocyclic aromatic group containing 1, 2 or 3 heteroatoms selected from nitrogen, oxygen and sulphur), said benzene ring (or in the case of naphthyl either benzene ring) being substituted by groups $R^2$ and $R^3$ which are ortho with respect to one another, wherein $R^2$ is hydroxy or an in vivo hydrolysable ester thereof and $R^3$ is hydroxy or an in vivo hydrolysable ester thereof, ii) a group of the formula (II):

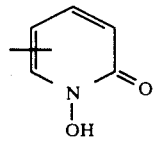

iii) a group of the formula (III):

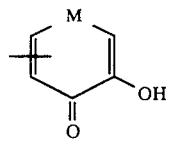

wherein M is oxygen or a group $NR^a$ wherein $R^a$ is hydrogen or $C_{1-6}$ alkyl, ring Q (or, in the case wherein ring Q is a benzene ring and is fused to another benzene ring, either benzene ring) is optionally substituted by $C_{1-6}$ alkyl, halo, hydroxy, hydroxy $C_{1-6}$ alkyl, cyano, trifluoromethyl, nitro, amino, $C_{1-6}$ alkylamino, di-$C_{1-6}$ alkylamino, amino $C_{1-6}$ alkyl, $C_{1-6}$ alkylamino $C_{1-6}$ alkyl, di-$C_{1-6}$ alkylamino $C_{1-6}$ alkyl, $C_{1-6}$ alkanoyl, $C_{1-6}$ alkoxy, $C_{1-6}$ alkylthio, $C_{1-6}$ alkanoyloxy, carbamoyl, $C_{1-6}$ alkylcarbamoyl, di-$C_{1-6}$ alkyl carbamoyl, carboxy, carboxy $C_{1-6}$ alkyl, sulpho, sulpho $C_{1-6}$ alkyl, $C_{1-6}$ alkanesulphonamido, $C_{1-6}$ alkoxycarbonyl, $C_{1-6}$ alkanoylamino, nitroso, thioureido, amidino, ammonium, mono-, di- or tri- $C_{1-6}$ alkylammonium or pyridinium, or a 5-membered heterocyclic ring containing 1 to 4 heteroatoms selected from oxygen, nitrogen and sulphur which is optionally substituted by 1, 2 or 3 $C_{1-6}$ alkyl or $C_{1-6}$ alkoxy groups;

$R^1$ is hydrogen, $C_{1-6}$ alkyl optionally substituted by any of halo, hydroxy, $C_{1-6}$ alkoxy, carboxy, amino, cyano, $C_{1-6}$ alkanoylamino, phenyl or heteroaryl, or $R^1$ is $C_{2-6}$ alkenyl;

Y is —CO— or —SO$_2$—;

Z is a direct bond, $C_{1-4}$ alkylene, $C_{2-4}$ alkenylene, $C_{2-4}$ alkynylene, —CO—, —(CH$_2$)$_n$NR$^4$CO— or —CONR$^4$(CH$_2$)$_n$—wherein n is 0 to 4;

$R^4$ is hydrogen or $C_{1-6}$ alkyl; and

A is optionally substituted benzene or an optionally substituted 5- or 6-membered heterocyclic ring containing 1, 2 or 3 ring atoms selected from nitrogen, oxygen and sulphur.

In one aspect $R^1$ may be $C_{1-6}$ alkyl substituted by heteroaryl. Suitably such a heteroaryl group is a 5- or 6-membered ring containing 1, 2 or 3 ring atoms selected from nitrogen, oxygen and sulphur and may be optionally substituted, for example by the substituents described hereinabove with respect to ring Q. For example $R^1$ may be pyridinylmethyl or furanylmethyl.

Particular meanings for $R^1$ are hydrogen, $C_{1-6}$ alkyl for example methyl, ethyl or propyl, hydroxy $C_{1-6}$ alkyl for example 2-hydroxyethyl, halo $C_{1-6}$ alkyl for example 2-chloroethyl or 2l -fluoroethyl, $C_{1-6}$ alkoxy $C_{1-6}$ alkyl for example 2-methoxyethyl, 2-ethoxyethyl or methoxymethyl, carboxy $C_{1-6}$ alkyl for example carboxymethyl, phenyl $C_{1-6}$ alkyl for example benzyl or phenethyl, or $C_{2-6}$ alkenyl for example allyl.

Preferably $R^1$ is hydrogen, methyl or ethyl. Most preferably $R^1$ is hydrogen.

In one aspect Y is —SO$_2$—forming a sulphonamide. Preferably Y is —CO—forming an amide.

In a particular aspect A is an optionally substituted benzene ring which links groups Y and Z. The substitution of groups Y and Z about the benzene ring may be ortho, meta or para. IN a preferred aspect the substitution is para.

In another particular aspect A is an optionally substituted 5- or 6-membered heterocyclic ring containing up to 3 ring atoms selected from nitrogen, oxygen and sulphur. Suitable rings A include pyridine, pyrimidine, pyrazine, pyridazine, imidazole, thiazole, oxazole, pyrrole, thiophen, thiazine, dihydroimidazole and tetrahydropyrrole. The present invention covers all possible substitution patterns of the groups Y and Z about the ring, for example the groups Y and Z can be linked via carbon and/or nitrogen atoms.

Particularly preferred rings A include 1,4-phenylene, 2,5-pyridylene, 3,4-pyridylene, 2,5-pyrimidylene, 1,2-pyridin-4-one, 1,4-pyridin-2-one, 1,3-pyridin-4-one, 1,2-tetrahydropyrrole and 1,3-dihydroimidazolin-2-one.

Optional substituents for ring A are as described hereinabove with respect to ring Q. In particular optional substituents for ring A include $C_{1-6}$ alkyl, halo, hydroxy, hydroxy $C_{1-6}$ alkyl, cyano, trifluoromethyl, nitro, amino, $C_{1-6}$ alkylamino, di-$C_{1-6}$ alkylamino, $C_{1-6}$ alkanoyl, $C_{1-6}$ alkoxy, $C_{1-6}$ alkylthio, $C_{1-6}$ alkanoyloxy, carbamoyl, $C_{1-6}$ alkylcarbamoyl, di-$C_{1-6}$ alkyl carbamoyl, carboxy, carboxy $C_{1-6}$ alkyl, $C_{1-6}$ alkoxycarbonyl $C_{1-6}$ alkyl, sulpho, sulpho$C_{1-6}$alkyl, sulphonamido $C_{1-6}$alkyl, $C_{1-6}$ alkoxycarbonyl, $C_{1-6}$ alkanoylamino, thioureido or amidino. In addition ring A may be fused to a benzene ring for example forming a naphthyl or quinoline group. In cases where a hydroxy substituent is present it may be possible to present ring A in tautomeric form with an oxo (—O) substituent. Thus, for the avoidance of doubt, the present invention covers such tautomeric forms, for example pyrimidinone, pyridinone, pyrazinone, pyridazinone, triazinone and the like, which as described hereinabove may be linked via carbon or nitrogen atoms.

In one aspect Z is a direct bond linking rings A and Q. In another aspect Z is —CO—or —(CH$_2$)$_n$—NR$^4$—CO—wherein the carbonyl group is linked to ring Q, R$^4$ is hydrogen or $C_{1-6}$ alkyl (for example methyl or ethyl) and n is 0 to 4. More particularly n is 0 or 1 and R$^4$ is hydrogen. In a further aspect Z is —CONR$^4$—(CH$_2$)$_n$—wherein the carbonyl group is linked to ring A, R$^4$ is hydrogen or $C_{1-6}$ alkyl (for example methyl or ethyl) and n is 0 to 4. More particularly n is 0 and R$^4$ is hydrogen. In another particular aspect Z is $C_{1-4}$ alkylene (for example methylene or ethylene), $C_{2-4}$ alkenylene (for example ethenylene) or $C_{2-4}$ alkynylene (for example ethynylene).

In one aspect Q is a benzene ring substituted by groups R$^2$ and R$^3$ as hereinbefore defined. R$^2$ is hydroxy or an in vivo hydrolysable ester thereof. In vivo hydrolysable esters are those pharmaceutically acceptable esters that hydrolyse in the human or animal body to produce the parent hydroxy compound. Such esters can be identified by administering, e.g. intravenously to a test animal, the compound under test and subsequently examining the test animal's body fluids. Suitable in vivo hydrolysable esters include $C_{1-6}$ alkanoyloxy for example acetoxy, propionyloxy, pivaloyloxy, $C_{1-4}$ alkoxycarbonyloxy for example ethoxycarbonyloxy, phenylacetoxy and phthalidyl, R$^3$ is hydroxy or an in vivo hydrolysable ester thereof.

Conveniently both R$^2$ and R$^3$ have the same value and are both hydroxy or are both in vivo hydrolysable esters, for example they are both acetoxy or both pivaloyloxy.

In one aspect Q is a ring of the formula (III). Suitably M is oxygen thus forming a pyranone ring. Suitably also M is —NR$^a$ wherein R$^a$ is hydrogen or $C_{1-6}$ alkyl in which case the linking group Z is attached to the pyridinone ring via a ring carbon atom or Z is linked to the nitrogen atom (replacing group R$^a$).

In a particular aspect Q is a benzene ring optionally fused to another benzene ring so forming a naphthyl group. As stated hereinbefore either benzene group may be substituted by R$^2$ and R$^3$ and by other optional substituents.

Particular optional substituents for Q are $C_{1-6}$ alkyl for example methyl, ethyl or isopropyl, halo for example chloro, bromo or fluoro, hydroxy, hydroxy $C_{1-6}$ alkyl for example hydroxyethyl, amino, $C_{1-6}$ alkylamino for example methylamino or ethylamino, di-$C_{1-6}$ alkylamino for example dimethylamino or diethylamino, nitro, $C_{1-6}$ alkylthio for example methylthio, $C_{1-6}$ alkoxy for example methoxy or ethoxy, carboxy $C_{1-6}$ alkyl for example carboxymethyl, $C_{1-6}$ alkanoylamino for example acetamido, trifluoromethyl, carboxy, carbamoyl, di-$C_{1-6}$alkylcarbamoyl for example dimethylcarbamoyl, $C_{1-6}$ alkylcarbamoyl for example methylcarbamoyl, cyano, $C_{1-6}$ alkanesulphonamido for example methanesulphonamido, $C_{1-6}$ alkanoyl for example acetyl, $C_{1-6}$ alkanoyloxy for example acetoxy or propionoxy and $C_{1-6}$ alkoxycarbonyl for example methoxycarbonyl. Of these, favoured substituents are bromo, chloro, fluoro, nitro, cyano and hydroxy.

The skilled man will realise that when Q is a benzene ring up to 3 optional substituents are possible and when a naphthyl ring is formed more substituents are possible and up to 2 to 3 optional substituents are possible with the rings of formulae (II) and (III). In general, we prefer up to 2 optional substituents, which may be the same or different.

Thus in a particular aspect, a preferred class of cephalosporin compounds of the present invention has a 3-position substituent of the formula (IV):

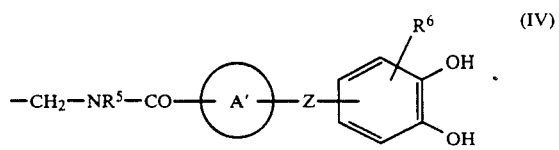

(IV)

or is an in-vivo hydrolysable ester thereof, wherein R$^5$ is hydrogen, methyl or ethyl, A$^1$ is 1,4-phenylene, 2,5-pyridylene, 3,4-pyridylene or 2,5-pyrimidylene, 1,3-pyridin-2-one, 1,2-pyridin-4-one, 1-3-dihydroimidazolin-2-one or 1,2-tetrahydropyrrole, Z is a direct bond, —NHCO—, —CONH—or —CH$_2$NHCO—, and R$^6$ is hydrogen, bromo, chloro, fluoro, nitro, cyano or hydroxy.

Particular substituents of the formula (IV) are:
2-(3,4-dihydroxyphenyl)pyridin-5-carboxamidomethyl,
2-(2-bromo-4,5-dihydroxyphenyl)pyridin-5-carboxamidomethyl,
4-(3,4-dihydroxyphenyl)pyridin-3-carboxamidomethyl,
2-(3,4-dihydroxyphenyl)-4-oxo-pyrimidin-5-carboxamidomethyl and
2-(3,4-diacetoxyphenylcarbamoyl)pyridin-5-carboxamidomethyl.

As stated hereinbefore the present invention relates to cephalosporins having a novel 3-position substituent. A particular class of cephalosporins within the present invention is that of the formula (V):

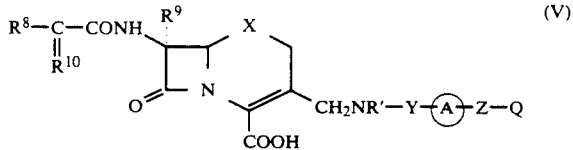

and salts and esters thereof wherein $R^1$, Y, A, Z and Q are as hereinbefore defined;

X is sulphur, oxygen, methylene or sulphinyl;

$R^9$ is hydrogen, methoxy or formamido; and $R^8$ and $R^{10}$ are groups known for such positions in the cephalosporin art.

Preferably X is sulphur,

Preferably $R^9$ is hydrogen.

$R^8$ is for example 2-aminothiazol-4-yl or 2-aminooxazol-4-yl each optionally substituted in the 5-position by fluorine, chlorine or bromine, or $R^8$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

$R^{10}$ is for example of the formula $=N.O.R^{11}$ (having the syn configuration about the double bond) wherein $R^{11}$ is hydrogen, (1-6C)alkyl, (3-8C)cycloalkyl, (1-3C)alkyl (3-6C)cycloalkyl, (3-6C)cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(-1-4C)alkyl, (1-4C)haloalkylcarbamoyl(1-4C)alkyl, (1-3C)haloalkyl, (2-6C)hydroxyalkyl, (1-4C)alkoxy(-2-4C)alkyl, (1-4C)alkylthio(2-4C)alkyl, (1-4C)alkanesulphinyl(1-4C)alkyl, (1-4C)alkanesulphonyl(1-4C)alkyl, (2-6C)aminoalkyl, (1-4C)alkylamino(1-6C)alkyl, (2-8C)dialkylamino(2-6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or $R^{11}$ is of the formula (VI):

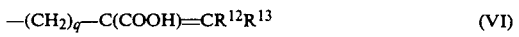

wherein q is one or two and $R^{12}$ and $R^{13}$ are independently hydrogen or $C_{1-4}$alkyl; or $R^{11}$ is of the formula (VII):

wherein r is 0–3, $R^{14}$ is hydrogen, (1-3C)alkyl or methylthio, $R^{15}$ is hydrogen (1-3C)alkyl, (3-7C)cycloalkyl, cyano, carboxy, (2-5C)carboxyalkyl or methanesulphonylamino, or $R^{14}$ and $R^{15}$ are joined to form, together with the carbon to which they are attached, a (3-7C)carbocyclic ring, and $R^{16}$ is hydroxy, amino, (1-4C)alkoxy, (1-4C) alkylamino or of the formula $NHOR^{17}$ in which $R^{17}$ is hydrogen or (1-4C)alkyl;

or $R^{10}$ may be of the formula $=CH.R^{18}$ wherein $R^{18}$ is hydrogen, halogen, (1-6C)alkyl, (3-7C) cycloalkyl, (2-6C)alkenyl, (3-7C)cycloalkenyl, phenyl or benzyl.

Particular meanings for $R^{11}$ are hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, 2-chloroethyl, 2-fluoroethyl, 2-bromoethyl, 2-hydroxyethyl, 3-hydroxypropyl, 2-methoxyethyl, 2-ethoxyethyl, 2-methylthio-ethyl, 2-methanesulphinylethyl, 2-methanesulphonyl-ethyl, 2-aminoethyl, 3-aminopropyl, 2-methylamino ethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)-ethyl, tetrahydropyran-2-yl, thietan-3-yl, 2-oxopyrrolidinyl and 2-oxotetrahydrofuran-3-yl, or, when $R^{11}$ is of the formula VI in which q is 1 or 2, a particular meaning for $R^{11}$ is when $R^{12}$ and $R^{13}$ are hydrogen or methyl, or, when $R^{11}$ is of the formula VII, a particular meaning for $R^{11}$ is when r=0 and $R^{14}$ is hydrogen, methyl or methylthio, $R^{15}$ is hydrogen, methyl, cyclopropyl, cyclobutyl, cyclopentyl, cyclohexyl, cyano, carboxy, carboxymethyl, 2-carboxyethyl or methanesulphonylamino, or when $R^{14}$ and $R^{15}$ are joined to form, together with the carbon to which they are attached, a cyclopropane, cyclobutane, cyclopentane, cyclohexane or cycloheptane ring and $R^{16}$ is hydroxy, amino, methoxy, ethoxy, methylamino, ethylamino, or of the formula $NHOR^{17}$ in which $R^{17}$ is hydrogen, methyl or ethyl.

Preferably $R^{11}$ is $C_{1-6}$alkyl for example methyl or ethyl, 1-carboxycyclobutyl, 1-carboxycyclopentyl, or 2-carboxyprop-2-yl. In particular $R^{11}$ is 2-carboxyprop-2-yl.

Particular meanings for $R^{18}$ are hydrogen, methyl, ethyl or chlorine.

It should be realised, of course, that the present invention covers all isomeric and tautomeric forms.

Particular meanings for $R^{18}$ are hydrogen, methyl, ethyl or chlorine.

As stated be hereinbefore the compounds of this invention are primarily intended for use in therapy. Therefore in a preferred aspect the present invention provides a cephalosporin compound having a 3-position substituent of the formula I or a pharmaceutically acceptable salt or ester thereof. Suitable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, or N,N-dibenzylethylamine.

In order to use a compound of the present invention or a pharmaceutically acceptable salt or ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a cephalosporin compound having a 3-position substituent of the formula I or a pharmaceutically acceptable salt or ester thereof and a pharmaceutically acceptable carrier.

The pharmaceutical compositions of this invention may be administered in standard manner for the disease condition that it is desired to treat, for example by oral, rectal or parenteral administration. For these purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the pharmaceutically acceptable cephalosporin derivative of the present invention the pharmaceutical composition of the invention may also contain, or be co-administered with, one or more known drugs selected from other clinically useful antibacterial agents (for example other beta-lactame or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 50% w/w or the cephalosporin derivative, or one suitable for oral administration in unit dosage form, for example a tablet or capsule which contains between 100 mg, and 1 g, of the cephalosporin derivative.

The pharmaceutical compositions of the invention will normally be administered to man in order to combat infections caused by bacteria, in the same general manner as that employed for cephalothin, cefoxitin, cephradine, ceftazidime and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.05 to 30 g., and preferably 0.1 to 10 g., of the cephalosporin derivative, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

In a further aspect the present invention provides a process for preparing a cephalosporin compound having a 3-position substituent of the formula I, which process comprises:

a) reacting a cephalosporin compound having a 3-position substituent of the formula: —CH$_2$NHR$^1$ wherein R$^1$ is as hereinbefore defined with a compound of the formula (VIII):

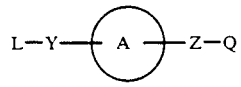
(VIII)

wherein R, A, Z and Q are as hereinbefore defined and L is a leaving group; or b) for compounds of the formula V, reacting a compound of the formula IX with a compound of the formula X or a reactive derivative thereof:

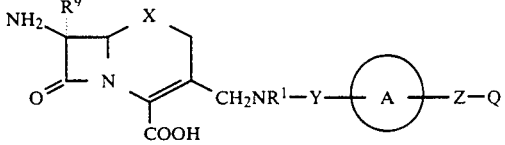
(IX)

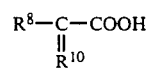
(X)

wherein R$^1$, Y, A, Z, Q, R$^9$, X, R$^8$ and R$^{10}$ are as hereinbefore defined; or c) for compounds of the formula V wherein R$^{10}$ is a group =NOR$^{11}$, reacting a compound of the formula XI:

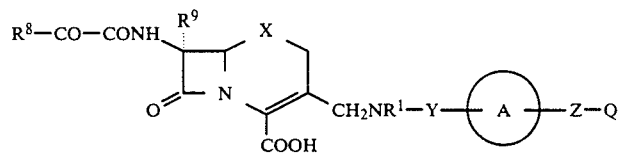
(XI)

wherein R$^1$, R$^8$, R$^9$, X, Y, Z, A and Q are as hereinbefore defined, with a compound of the formula: R$^{11}$ONH$_2$ wherein R$^{11}$ is as hereinbefore defined; or d) for compounds of the formula V wherein R$^{10}$ is a group =NOR$^{11}$ and R$^{11}$ is other than hydrogen, reacting a compound of the formula V as hereinbefore defined wherein R$^{10}$ is a group =NOH with a compound of the formula XII:

L$^1$—R$^{19}$ (XII)

wherein L$^1$ is a leaving group and R$^{19}$ is a group R$^{11}$ other than hydrogen; or e) for compounds of the formula V wherein R$^8$ is a cyclic group, forming a group R$^8$ by cyclizing an appropriate precursor thereof: wherein any functional groups are optionally protected; or f) reaction of a cephalosporin derivative having a group of the formula (XIII) at the 3-position with a compound of the formula (XIV):

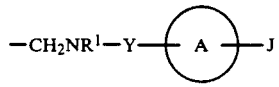
(XIII)

X—Q (XIV)

wherein J and K in the above formulae are such that reaction takes place to form the link Z between the rings A and Q,
and thereafter, if necessary:

i) removing any protecting group, ii) for preparing in vivo hydrolysable esters, esterifying corresponding hydroxy groups, iii) converting compounds wherein X is S to compounds wherein X is sulphinyl and vice versa, iv) forming a pharmaceutically acceptable salt.

In the reaction between a cephalosporin compound having a 3-position substituent of the formula: —CH$_2$NHR$^1$ and a compound of the formula VIII, conveniently L is a leaving group such as halo for example chloro, bromo or iodo. Most suitably the reaction is performed under conditions conventional for the reaction of acid halides with amines for example in the presence of an organic amine or coupling reagents such as dicyclohexylcarbodiimide and hydroxybenztriazole. Suitably the reaction is performed at an ambient or lower temperature in a substantially inert solvent such as dimethylformamide and/or dichloromethane. In an alternative aspect the leaving group L is part of an activated ester formed with the acid precursor of the compound of the formula VIII, i.e. a compound wherein L is —OH provides an activated ester, e.g. dicyclohexylcarbodi-imide provides an activated ester of the formula VII wherein L is —OC(NHC$_6$H$_{11}$)=NC$_6$H$_{11}$, which group is displaced by the cephalosporin having a 3-position substituent of the formula: —CH$_2$NHR$^1$. Formation and reaction of the active ester is performed in conventional manner in the presence of reaction promotors such as hydroxybenzotriazole and triethylamine, for example in a substantially inert organic solvent such as dimethylformamide at a non-extreme temperature such as 10°–50° C.

The cephalosporin starting-materials for this reaction are known from the art, or are made by methods analogous to those of the art. See for example EP-A-127992 and EP-A-164944.

The compounds of the formula VIII are either known in the art or are made by methods analogous thereto. For example compounds wherein L is chloro are conveniently prepared from the corresponding acids. The acids are known or are prepared by methods of heterocyclic chemistry known to those skilled in the art, for example as in the hereinafter described Examples.

The reaction between compounds of the formulae IX and X is performed under conditions conventional in the cephalosporin art, for example under standard acylation conditions wherein for example the acid is activated as an acid bromide, acid chloride, anhydride or activated ester, or the reaction is performed in the presence of a coupling reagent such as dicyclohexylcarbodiimide.

The compounds of the formula IX can be prepared in a manner analogous to that described for the compounds of the formula I, with the 7-amino group being optionally protected.

The reaction between compounds of the formula XI and R$^{11}$ONH$_2$ is performed under conditions standard in the general chemical and/or cephalosporin art. The compounds of the formula XI can be prepared in a manner analogous to that described for the compounds of the formula I.

The reaction between the compound of the formula V wherein R$^{10}$ is a group =NOH and a compound of the formula XII is performed under conditions standard in the general chemical and/or cephalosporin art.

A group R$^8$ may be formed by cyclizing an appropriate precursor. For example compounds of the formulae XV and XVI:

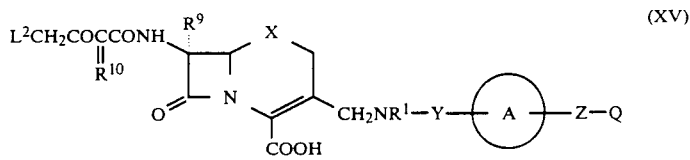

wherein R$^1$, R$^9$, R$^{10}$, A, X, Y, Z and Q are as hereinbefore defined and L$^2$ is a leaving group, may be reacted to form a 2-aminothiazol-4-yl group. A nitrogen atom of the thiourea may be optionally protected during this cyclization.

The compounds of the formula XV can be prepared in a manner analogous to that described for the compounds of the formula I.

In the formulae XIII and XIV, particular meanings for J and K include for example wherein J is —(CH$_2$)$_n$NH$_2$ and K represents —COCl or —COOH which react together to form a link —(CH$_2$)$_n$NHCO—. Another example is wherein J is H (such as part of a —NH—containing ring) and K is —COCl in which case the link —CO—is formed.

The compounds of the formulae X, XII and R$^{11}$ONH$_2$ are known from, or can be made by the methods of the general chemical and/or cephalosporin art.

The compounds of the formulae IX, XI and XV are novel and as such form a further aspect of the present invention.

In the process of this invention any functional group can be optionally protected, if appropriate. Such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol, silanol or stannanol (the said alcohol, phenol, silanol or stannanol preferably containing 1-20 carbon atoms).

Examples of carboxyl protecting groups include straight or branched chain (1-12C)alkyl groups (e.g. isopropyl, t-butyl); halo lower alkyl groups (e.g. 2-iodoethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxy-carbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, base-, metal- or enzymically-catalysed hydrolysis.

Examples of hydroxyl protecting groups include lower alkanoyl groups (e.g. acetyl); lower alkoxycarbonyl groups (e.g. t-butoxycarbonyl); halo lower alkoxycarbonyl groups (e.g. 2-iodoethoxycarbonyl, 2,2,2-trichloroethoxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl) and aryl lower alkyl (e.g. benzyl) groups. In addition two hydroxy groups substituted on adjacent carbon atoms, for example in the catechol moiety, may be protected in the form of a cyclic acetal such as the methylenedioxy moiety.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; acyl (e.g. alkoxycarbonyl and aralkoxycarbonyl e.g. t-butoxycarbonyl and benzyloxycarbonyl); trialkylsilyl (e.g. trimethylsilyl and t-butyldimethylsilyl); alkylidene (e.g. methylidone); benzylidene and substituted benzylidene groups; and the phthalimido group.

The following biological test methods, data and Examples serve to illustrate this invention.

Antibacterial Activity

The pharmaceutically acceptable cephalosporin compounds of the present invention are useful antibacterial agents having a broad spectrum of activity in vitro against standard laboratory microorganisms, both Gram-negative and Gram-positive, which are used to screen for activity against pathogenic bacterial. The antibacterial spectrum and potency of a particular compound may be determined in a standard test system. The compounds have particularly high activity in vitro against strains of Pseudomonas aeruginosa.

The antibacterial properties of the compounds of the invention may also be demonstrated in vivo in conventional mouse protection tests.

Cephalosporin derivatives have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Isosensitest agar medium. The antibacterial activity is described in terms of the minimum inhibitory concentration (MIC) determined by the agar-dilution technique with an inoculum size of $10^4$ CFU/spot.

| ORGANISM | MIC (μl/ml) EXAMPLE | | | | |
|---|---|---|---|---|---|
| | 1 | 2 | 3 | 4 | 7 |
| P. aeruginosa PU21 (A8101028) | 0.06 | 0.03 | 0.25 | 0.015 | 0.06 |
| Ent. cloacae P99 (A8401054) | 0.06 | 0.125 | 1 | 0.25 | 0.25 |
| Serr. marcesens (A8421003) | 0.03 | 0.015 | 0.5 | 0.06 | 0.06 |
| Pr. morganii (A8433001) | 0.25 | 0.06 | 1 | 0.06 | 0.25 |
| Kleb. aerogenes (A8391027) | 0.008 | 0.008 | 0.06 | 0.008 | 0.015 |
| E. coli DCO (A8341098) | 0.008 | 0.008 | 0.06 | 0.008 | 0.008 |
| St. aureus 147N (A8601052) | 4 | 8 | 64 | 16 | 16 |
| S. dublin (A8369001) | 0.03 | 0.008 | 0.125 | 0.015 | 0.06 |
| Strep. pyogenes (A681018) | 0.03 | 0.125 | 0.5 | 0.5 | 0.125 |

EXAMPLE 1

7-[2-(2-Aminothiazol-4-yl)-2-((Z)-1-carboxy-1-methylethoxyimino)acetamido]-3-(2-(3,4-dihydroxyphenyl)-pyridin-5-carboxamidomethyl)ceph-3-em-4-carboxylic acid

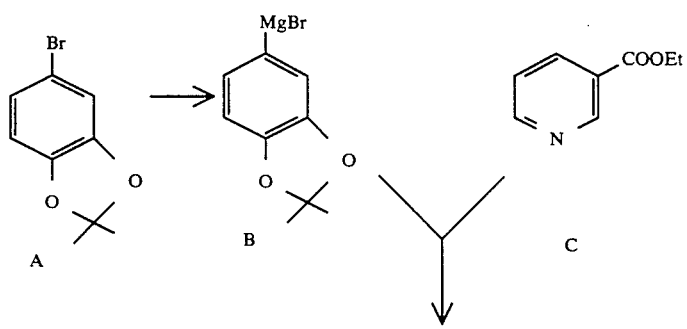

-continued
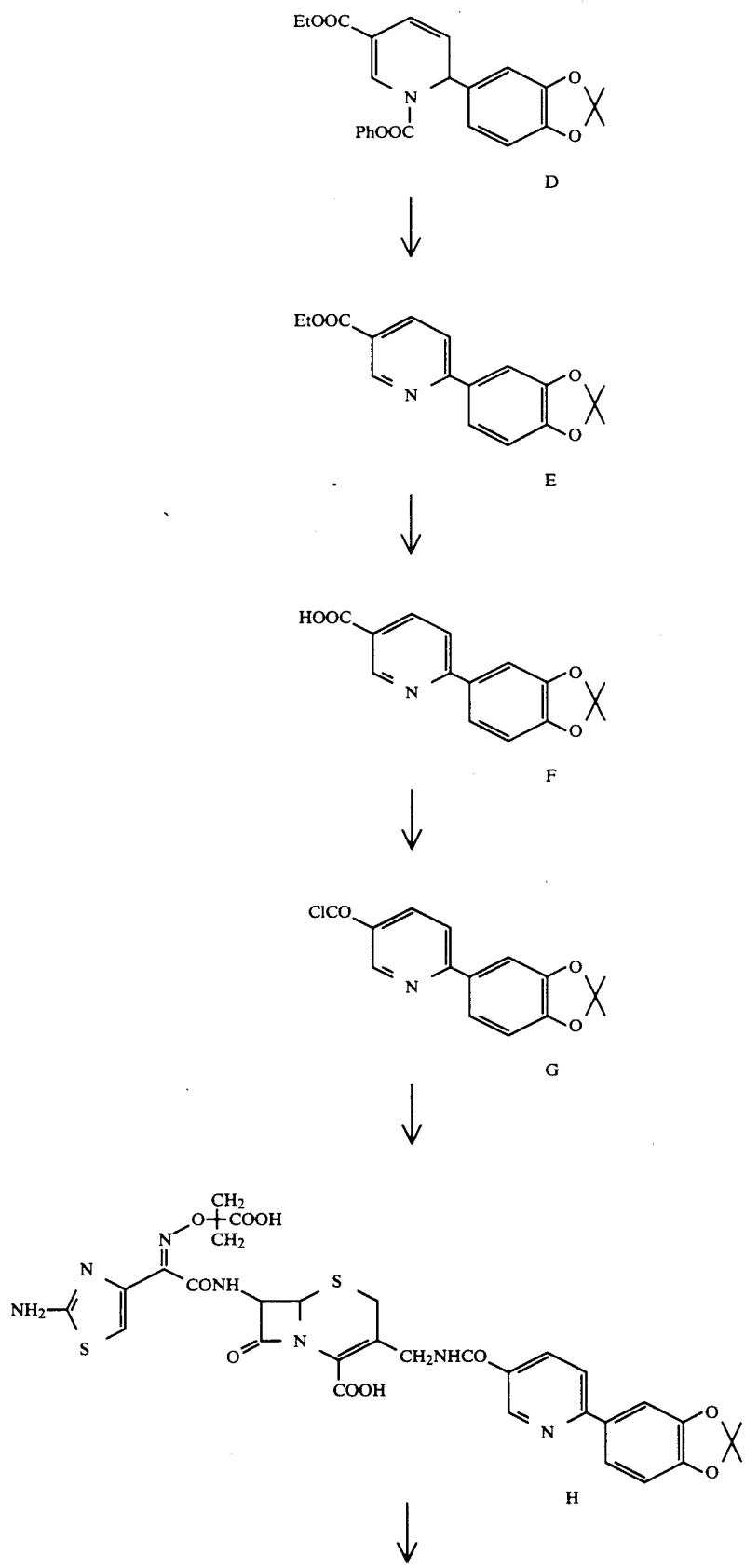

-continued

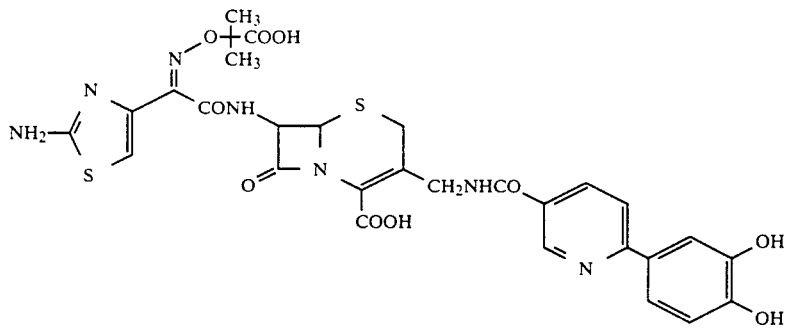

20

25

Compound H (143 mg) was dissolved in trifluoroacetic acid (10 ml) and stirred at ambient temperature for 16 hours. The solvent was removed under reduced pressure to give a yellow solid which was purified by preparative HPLC using acetonitrile/water/trifluoroacetic acid (20:80:0.1) as eluant. The title product (61 mg) was obtained after freeze-drying, as the trifluoroacetate salt; NMR 1.42 (s,3H0; 1.45(s,3H); 3.66 and 3.48(dd,2H); 4.19 and 4.54(dd,2H); 5.15(d,1H); 5.82(d,1H); 6.88(s,1H); 6.88(d,1H); 7.40 and 7.44(dd,1H); 7.59(d,1H); 7.9(d,1H); 8.23 and 8.28(dd,1H); 8.99(d,1H); M/S 698 (M+H)+.

Compound H was prepared in the following manner:

(i) The acetonide A (3g) and magnesium turnings (1.06 g) in tetrahydrofuran (10 ml) were heated to 50° C. An iodine crystal was added and subsequently further acetonide A (7.08 g) dropwise. The resultant solution was cooled and stirred for 30 minutes to give a solution of compound B. Tetrahydrofuran (10 ml) was added and this solution was carefully added to a stirred solution of ethyl nicotinate (C) (6.04 g) in tetrahydrofuran (125 ml) maintained at −20° C. Phenylchloroformate (6.26 g) was added over 6 minutes, at −20° C., and the mixture was allowed to rise to ambient over 2 ½ hours. The mixture was diluted with aqueous ammonium chloride (250 ml) and ether (500 ml) and the ether phase was washed with dilute HCl, water and brine, dried and evaporated under reduced pressure to give intermediate D as an oil (13.61 g).

(ii) o-Chloranil (4.34 g) in glacial acetic acid (32 ml) was added to a solution of intermediate D (6.8 g) in toluene (75 ml) and left to stir for 72 hours. The solution was diluted with ether (100 ml), cooled, aqueous NaOH (250 ml) was added and the mixture was stirred for a further 15 minutes before being filtered through diatomaceous earth. The filtrate was separated, the organic layer washed with water and extracted into 14% HCl (4×100 ml). The combined acidic extracts were cooled, NaOH (78 g in 300 ml water) was added and the mixture was extracted into ether (2×200 ml). The ether extracts were washed with brine, dried and evaporated under reduced pressure to give intermediate E as an oil (972 mg). This was combined with material from another preparation (820 mg) and purified using "dry-column" flash chromatography eluting with ether/hexane to give a yellow oil (1.4 g) which crystallised on standing.

iii) To intermediate E (1.33 g) in ethanol (35 ml) was added 2N NaOH (2.5 ml). The mixture was stirred for 3 hours and evaporated under reduced pressure to give a solid which was dissolved in water (80 ml) and washed with ether. The pH of the aqueous layer was taken to 3.9 with glacial acetic acid whereupon a light yellow precipitate appeared. The mixture was extracted into ethyl acetate, dried and evaporated to give compound F (1.05 g) as a yellow solid; NMR (DMSO-d6) 1.7(s,6H); 6.96(d,1H); 7.62(d,1H); 7.69 and 7.72(dd,1H); 7.98 and 8.02(dd,1H); 8.23 and 8.28(dd,1H); 9.08(dd,1H); M/S 271 M+.

iv) To a suspension of compound F (298 mg) in dichloromethane (2 ml) and dimethylformamide (10μl), under argon, was added oxalyl chloride (190μl) dropwise over 3 minutes. The mixture was stirred for 20 minutes and evaporated under reduced pressure to give the acid chloride as an orange solid. This was dissolved in dichloromethane (3 ml) and coupled by adding dropwise over 5 minutes to a stirred suspension of 3-aminomethyl-7-[2-(2-aminothiazol-4-yl)-2-((Z)-1-carboxy-1-methylethoxyimino)acetamido]ceph-3-em-4-carboxylic acid (670 mg) in methanol (8 ml) and triethylamine (0.49 ml), under argon, at −15° C. The mixture was stirred for 2 hours and the solvent removed under reduced pressure to give a yellow solid which was purified by preparative HPLC eluting with acetonitrile/water/trifluoroacetic acid (35:65:0.1) to give compound H (153 mg); NMR (DMSO-d6/CD3COOD) 1.43(s,3H); 1.45(s,3H); 1.67(s,6H); 3.48 and 3.66(dd,2H); 4.2 and 4.57(dd,2H); 5.15(d,1H); 5.82(d,1H); 6.85(s,1H); 6.93(d,1H); 7.59(d,1H); 7.62 and 7.68(dd,1H); 7.95(d,1H); 8.2 and 8.25(dd,1H); 9.1(d,1H).

EXAMPLES 2-3

In a manner similar to Example 1, the following compounds were obtained:

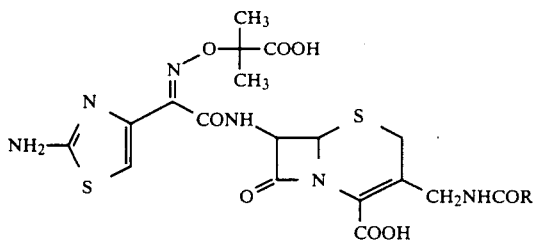

| Example | R | Footnote | NMR (DMSO-d$_6$/CD$_3$COOD) |
|---|---|---|---|
| 2 | 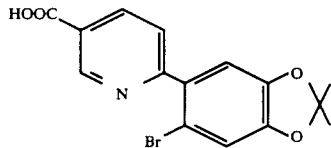 | 1 | 1.48(s, 3H); 1.50(s, 3H); 3.48 and 3.67(dd, 2H); 4.20 and 4.53(dd, 2H); 5.14(d, 1H); 5.82(d, 1H); 6.89(s, 1H); 7.06(s, 1H); 7.67 and 7.71(dd, 1H); 8.22 and 8.27(dd, 1H); 9.03(dd, 1H). |
| 3 | 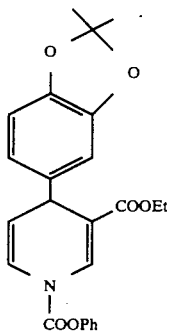 | 2 | 1.44(s, 3H); 1.49(s, 3H); 3.13 and 3.34(dd, 2H); 3.92 and 4.52(dd, 2H); 5.08(d, 1H); 5.83(d, 1H); 6.83(s, 3H); 6.97(s, 1H); 7.63(d, 1H); 8.65(d, 1H); 8.68(s, 1H). |

Footnotes

1. Compound F (see Example 1) was reacted with N-bromosuccinimide in dimethylformamide to form the bromo acetonide:

```
HOOC
    \
     \___
     /   \
    N     \___OH
         /    \
        Br     OH (acetonide)
```

The corresponding acid chloride was formed, coupled and the product deprotected as in Example 1.

2. The Grignard reaction was performed as in Example 1 with the addition of copper iodide to direct substitution to the 4-position of the ethyl nicotinate to give:

```
(acetonide-protected catechol)–(dihydropyridine with COOEt at 3-position, N-COOPh)
```

This product was treated with o-chloranil, hydrolysed to form the acid, the corresponding acid chloride was formed, coupled and the product deprotected as in Example 1.

7-[2-(2-Aminothiazol-4-yl)-2-((Z)-1-carboxy-1-methylethoxyimino)acetamido]-3-(2-(3,4-dihydroxyphenyl)-pyridin-4-oxopyrimidin-5-carboxamidomethyl)ceph-3-em-4-carboxylic acid

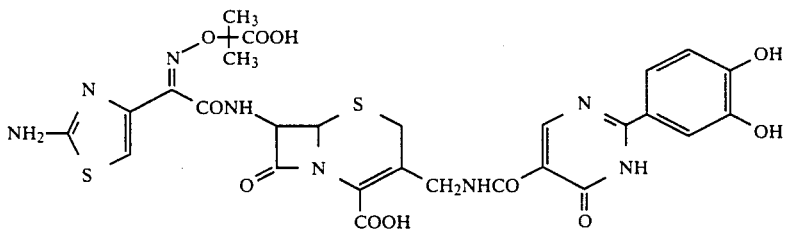

2-(3,4-Dihydroxyphenyl)-4-oxopyrimidin-5-carboxylic acid (124 mg) was suspended in dichloromethane (5 ml), treated successively with trimethylsilylchloride (217 mg) and triethylaine (202 mg) and stirred at ambient for 1 hour. Thionyl chloride (60 mg) and triethylamine (50 mg) were added and the mixture stirred, at room temperature, for a further hour and then evaporated under reduced pressure. The residue was dissolved in dimethylformamide (5 ml) and added to a solution of 3-aminomethyl-7-[2-(2-aminothiazol-4-yl)-2-[(Z)-1-carboxy-1-methylethoxyimino)acetamido]ceph-3-em-4-carboxylic acid (242 mg) and triethylamine (100 mg) in dimethyl formamide (5 mg) at room temperature. After stirring for 2 hours the reaction mixture was poured into water, the precipitated solid filtered off and the filtrate applied to a Diaion HP20SS resin column. The column was subjected to gradient elution ($H_2O$ to 10% $CH_2CN/H_2O$), the appropriate fractions combined, the acetonitrile removed under reduced pressure and the title product (45 mg) isolated by freeze-drying; NMR (DMSO-$d_6$/CD$_3$COOD) 1.41(s,3H); 1.42(s,3H); 3.49(d,1H); 3.67(d,1H); 4.02(d,1H); 4.47(d,1H); 5.1(d,1H); 5.82(d,1H); 6.72(s,1H); 6.87(d,1H); 7.58(dd,1H); 7.66(d,1H); 8.68(s,1H); M/S 713 (M+H)+.

2-(3,4-Dihydroxyphenyl)-4-oxopyrimidin-5-carboxylic acid was prepared in the following manner:

i) 3,4-Dihydroxyphenyl)-4-oxopyrimidin-5-carboxylic acid was prepared in the following manner:

NP20SS. The product 3,4-dihydroxybenzamidine hydrochloride, was obtained in 62% yield; NMR (DMSO-$d_6$/CD$_3$COOD) 6.95(d,1H0; 7.19–7.25(m,2H); 8.77(s,1H); 9.05(s,1H); M/S m/e 152 M+.

ii) 3,4-Dihydroxybenzamidine hydrochloride (3.5 g) was suspended in ethanol (10 ml) and treated with sodium ethoxide (prepared from sodium (0.43 g) and ethanol (13 ml)). The stirred mixture was cooled in an ice bath and treated dropwise with a solution of diethylethoxymethylene malonate (4.01 g) in ethanol (5 ml). The ice bath was removed and the mixture heated under reflux for 3 hours. During this time a yellow solid separated from solution. The reaction mixture was poured on to ice, acidified with conc. HCl (pH1) and the yellow solid filtered off. Recrystallisation from dimethylformamide gave ethyl 2-(3,4-dihydroxyphenyl)-4-oxopyrimidin-5-carboxylate (1.09 g); NMR (DMSO-$d_6$) 1.3(t,3H); 4.25(q,2H); 6.85(d,1H); 7.6(dd,1H); 7.65(d,1H); 8.5(s,1H): MS m/e 276 (M+).

iii) Ethyl 2-(3,4-dihydroxyphenyl)-4-oxopyrimidin-5-carboxylate (750 mg) and 1N NaOH (7.5 ml) was mixed and heated under reflux for 20 minutes. After being allowed to cool to room temperature the mixture was acidified with 2N HCl and the desired product which precipitated was filtered off, washed with water, and dried under vacuum (750 mg; mpt 301–303); NMR (DMSO-$d_6$) 6.81(d,1H); 7.5–7.6(m,2H); 8.54(s,1H).

EXAMPLE 5

7-[2-(2-Aminothiazol-4-yl)-2-((Z)-1-carboxy-1-methylethoxyimino)acetamido]-3-(2-(3,4-diacetoxyphenylcarbamoyl)-pyridin-5-carboxamidomethyl)ceph-3-em-4-carboxylic acid

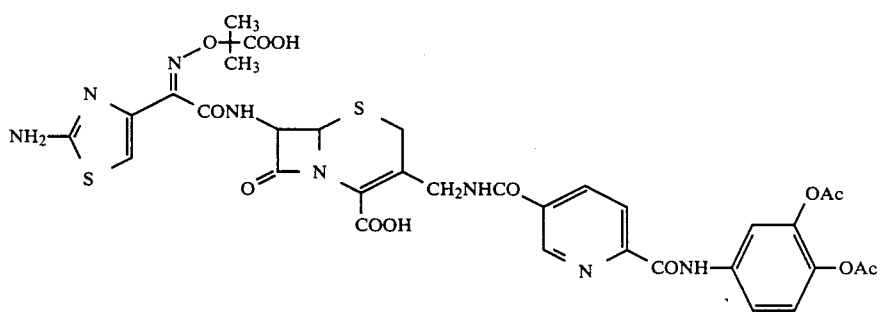

i) 3,4-Dihydroxybenzonitrile (0.5 g) was dissolved in ethanol (5 ml), and treated with a slow stream of HCl gas for 20 minutes before being left in a stoppered flask for 16 hours. The precipitated solid was filtered off, transferred in ethanol (20 ml) to a flash and the solution saturated with anhydrous ammonia. After stirring at room temperature for 6 hours the flask was stored in the fridge overnight. The solvent was evaporated under reduced pressure, the residue acidified (pH1) with conc. HCl, and purified by chomatography on Dianion In a manner similar to that of Example 1, 6-(3,4-diacetoxyphenylcarbamoyl)pyridine-3-carboxylic acid was converted to the corresponding acid chloride and coupled to give the title product; NMR (DMSO-$d_6$/CD$_3$COOD) 1.43(s,3H); 1.45(s,3H); 2.22(s,3H); 2.24(s,3H); 3.48 and 3.68(dd,2H); 4.20 and 5.49(dd,2H); 5.14(d,1H); 5.32(d,1H); 6.81(s,1H); 7.22(d,1H); 7.75 and 7.79(dd,1H); 7.91(d,1H); 8.22(d,1H); 8.40 and 8.45(dd,1H); 9.09(d,1H); MS 825 (M+H)+.

i) 6-(3,4-Diacetoxyphenylcarbamoyl)pyridine-3-carboxylic acid was prepared in standard manner according to the following Scheme:

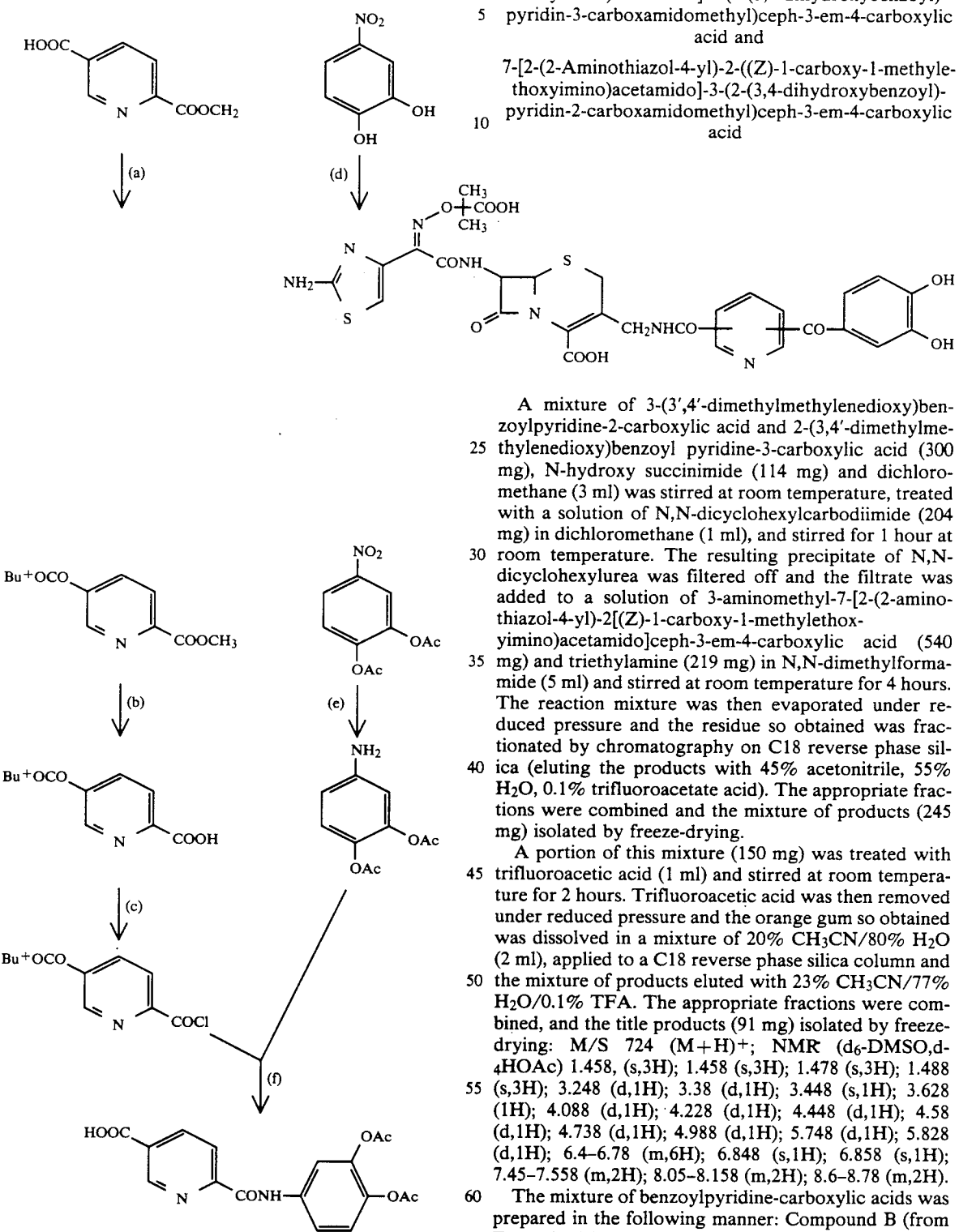

(a) Dimethylformamide t-butyl acetal/toluene/100° C.;
(b) NaOH/C₂H₅OH;
(c) Oxalyl chloride/dimethylformamide;
(d) Acetic anhydride/pyridine;
(e) Palladium on carbon/H₂/C₂H₅OH;
(f) Triethylamine/dichloromethane.

EXAMPLE 6

7-[2-(2-Aminothiazol-4-yl)-2-((Z)-1-carboxy-1-methylethoxyimino)acetamido]-3-(2-(3,4-dihydroxybenzoyl)-pyridin-3-carboxamidomethyl)ceph-3-em-4-carboxylic acid and 7-[2-(2-Aminothiazol-4-yl)-2-((Z)-1-carboxy-1-methylethoxyimino)acetamido]-3-(2-(3,4-dihydroxybenzoyl)-pyridin-2-carboxamidomethyl)ceph-3-em-4-carboxylic acid A mixture of 3-(3',4'-dimethylmethylenedioxy)benzoylpyridine-2-carboxylic acid and 2-(3,4'-dimethylmethylenedioxy)benzoyl pyridine-3-carboxylic acid (300 mg), N-hydroxy succinimide (114 mg) and dichloromethane (3 ml) was stirred at room temperature, treated with a solution of N,N-dicyclohexylcarbodiimide (204 mg) in dichloromethane (1 ml), and stirred for 1 hour at room temperature. The resulting precipitate of N,N-dicyclohexylurea was filtered off and the filtrate was added to a solution of 3-aminomethyl-7-[2-(2-aminothiazol-4-yl)-2[(Z)-1-carboxy-1-methylethoxyimino)acetamido]ceph-3-em-4-carboxylic acid (540 mg) and triethylamine (219 mg) in N,N-dimethylformamide (5 ml) and stirred at room temperature for 4 hours. The reaction mixture was then evaporated under reduced pressure and the residue so obtained was fractionated by chromatography on C18 reverse phase silica (eluting the products with 45% acetonitrile, 55% H₂O, 0.1% trifluoroacetate acid). The appropriate fractions were combined and the mixture of products (245 mg) isolated by freeze-drying.

A portion of this mixture (150 mg) was treated with trifluoroacetic acid (1 ml) and stirred at room temperature for 2 hours. Trifluoroacetic acid was then removed under reduced pressure and the orange gum so obtained was dissolved in a mixture of 20% CH₃CN/80% H₂O (2 ml), applied to a C18 reverse phase silica column and the mixture of products eluted with 23% CH₃CN/77% H₂O/0.1% TFA. The appropriate fractions were combined, and the title products (91 mg) isolated by freeze-drying: M/S 724 (M+H)⁺; NMR (d₆-DMSO,d-4HOAc) 1.458, (s,3H); 1.458 (s,3H); 1.478 (s,3H); 1.488 (s,3H); 3.248 (d,1H); 3.38 (d,1H); 3.448 (s,1H); 3.628 (1H); 4.088 (d,1H); 4.228 (d,1H); 4.448 (d,1H); 4.58 (d,1H); 4.738 (d,1H); 4.988 (d,1H); 5.748 (d,1H); 5.828 (d,1H); 6.4–6.78 (m,6H); 6.848 (s,1H); 6.858 (s,1H); 7.45–7.558 (m,2H); 8.05–8.158 (m,2H); 8.6–8.78 (m,2H).

The mixture of benzoylpyridine-carboxylic acids was prepared in the following manner: Compound B (from Example 1) in tetrahydrofuran (10 ml) was added dropwise over 10 minutes to 2,3-pyridinedicarboxylic acid anhydride (1.49 g) in tetrahydrofuran (10 ml) at 0° C. under argon. The mixture was stirred at 0° C. for 10 minutes and at ambient temperature for 1 hour. The mixture was diluted with saturated ammonium chloride (25 ml) and water (25 ml) extracted into ethyl acetate (100 ml). The organic phase was extracted with 2N sodium hydroxide (2×20 ml), these extracts were acidified with conc. HCl to pH2 and chromatographed on silica (eluting with ethyl acetate) to give the mixture of butoxycarbonyl-1-methylethoxyimino)acetamido]ceph-3-em-4-carboxylic acid with the appropriate sulphonyl chloride wherein the hydroxy groups were protected as acetoxy derivatives.

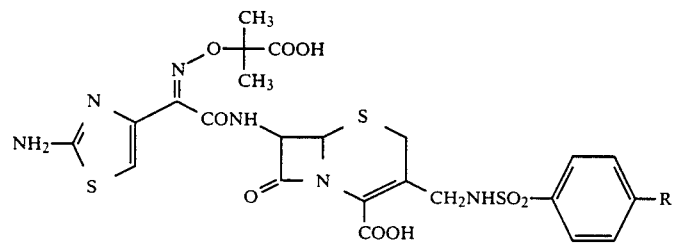

| Example | R | Footnote | NMR (DMSO-d$_6$/CD$_3$COOD) |
|---|---|---|---|
| 7 | —CH$_2$NHCO—[3,4-dihydroxyphenyl] | 1, 2, 3 | 1.46(d, 6H); 3.3–3.57(m, 2H); 3.6–4.1(m, 2H); 4.50(br s, 2H); 4.96(d, 1H); 5.82(d, 1H); 6.74(s, 1H); 6.77(d, 1H); 7.25(dd, 1H); 7.34(d, 1H); 7.47(d, 1H); 7.73(d, 1H). |
| 8 | —NHCO—[5-bromo-2,3-dihydroxyphenyl] | 1, 2, 3 | 1.45(d, 6H); 3.3–3.5(m, 2H); 3.65(d, 1H); 4.03(d, 1H); 4.92(d, 1H); 5.78(d, 1H); 6.77(s, 1H); 7.12(d, 1H); 7.55(d, 1H); 7.56(d, 2H); 7.88(d, 2H). |

Footnotes

1. To a suspension of the cephalosporin (0.5 mM) in dimethylformamide (6 ml) at 0° C. was added triethylamine (1.0 mM) followed by the appropriate sulphonyl chloride (0.5 mM) in dichloromethane (3 ml). The reaction mixture was stirred at 0° C. for 2 hours and at 22° C. for 1 hour. The mixture was poured on to ice-cold water (25 ml) and the pH was adjusted to 3.5 with 2N HCl. The mixture was extracted into dichloromethane and evaporated under reduced pressure to give an oil that was purified by chromatography on Diaion HP2OSS eluting with an acetonitrile:water gradient. The appropriate fractions were combined and concentrated to give a gum which was triturated with ether to afford an amorphous solid.

2. The product was stirred with 90% trifluoroacetic acid at 0° C. for 2 hours to remove the tert-butoxy group. The solvent was evaporated, the residue diluted with water and the acetoxy groups hydrolysed by the dropwise addition of 5% ammonia at pH 8.7.

3. The sulphonyl chlorides were prepared by reacting 3,4-diacetoxybenzoylchloride with aniline (or benzylamine) in dichloromethane in the presence of triethylamine, and subsequently heating the product at 60° C. with chlorosulphonic acid. The sulphonyl chloride (which may have been partially deprotected) was not purified but reacted in situ with the cephalosporin.

carboxylic acids (0.27 g) as a pale, brown solid; NMR (CDCl$_3$/DMSO-d$_6$) 1.64 (s,6H); 6.69 (d,1H); 7.14 (dd,1H); 7.20 (s,1H); 7.48 (dd,1H); 8.32 (dd,1H); 8.70 (dd,1H); MS m/e 299 M+.

EXAMPLES 7 and 8

The following compounds were prepared by reacting 3-aminomethyl 7-[2-(2-aminothiazol-4-yl)-2((Z)-1-tert-

EXAMPLE 9

7-[2-(2-Aminothiazol-4-yl)-2-((Z)-1-methoxyethoxyimino)acetamido]-3-(1,2-dihydro-1(3,4-dihydroxybenzyl)-3-hydroxy-2-oxoquinolin-4-carboxamidomethyl)-ceph-3-em-4-carboxylic acid

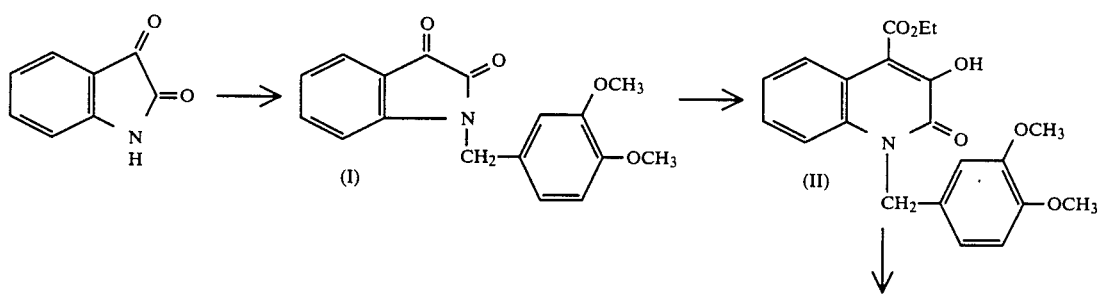

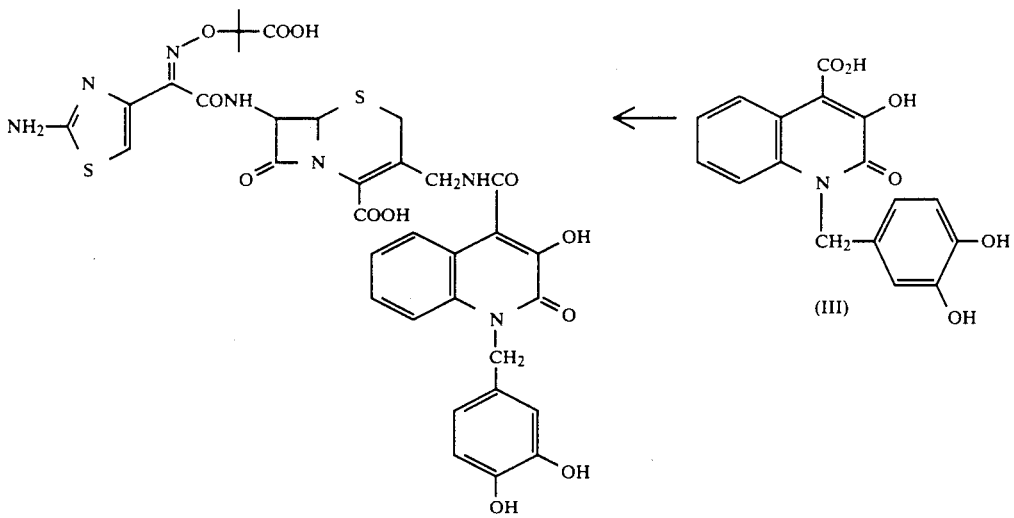

Trimethylsilylchloride (382 μl: 3mM) was added to a stirred suspension of compound III (164 mg; 0.5 mM) in chloroform (4 ml) under an atmosphere of argon. Triethylamine (416 μl; 3 mM) was added and the mixture was stirred for 30 minutes. Thionyl chloride (40 μl; 0.55 mM), triethylamine (76 μl; 0.55 mM) and dimethylformamide (5 μl) were added and the mixture stirred for a further two hours. This solution was then added to a cooled (ice/water bath) solution of silylated 3-aminomethyl-7-[2-(2-aminothiazol-4-yl)-2-((Z)-1-carboxy-1-methylethoxyimino)acetamido]ceph-3-em-4-carboxylic acid under an atmosphere of argon. The mixture was stirred at 0° C. for 15 minutes, at room temperature for 100 minutes and evaporated under reduced pressure to give, on trituration with water, a yellow solid (446 mgs). This was purified by HPLC (Dynamax Macro column; $C_{18}$; 8μm; 250×21 mm; eluent 27% aqueous acetonitrile/0.1 trifluoroacetic acid) to give the title product; NMR (DMSO-$d_6$/$CF_3COOH$) 1.53 (s,3H); 1.56 (s,3H); 3.55(d,1H); 3.75(d,1H); 4.19 and 4.24(dd,1H); 4.54 and 4.60(dd,1H); 5.19(d,1H); 5.41(brs,2H); 5.83 and 5.86(dd,1H); 6.55(m,2H); 6.66(d,1H); 7.0-7.5(m,3H); 7.08(s,1H); 8.85 and 8.90(dd,1H); 9.7(d,1H).

The silylated cephalosporin starting material was prepared by treating a stirred suspension of the corresponding free acid (0.5 mM) in dichloromethane (20 ml) with trimethylsilylchloride (4.5 mM) under an atmosphere of argon. Subsequently triethylamine (4.5 mM) was added and the mixture stirred for 30 minutes to give a solution.

Compound III was prepared as follows:

i) Potassium hydroxide (4.76 g) in ethanol (85 ml) was added to isatin (11.73 g) in dimethylsulphoxide (80 ml) and the mixture was stirred for 10 minutes. 3,4-Dimethoxybenzyl chloride (0.1 M) was added, the mixture was stirred overnight and poured into water (1600 ml) to give a precipitate. This was collected and crystallised from propan-2-ol to give compound I (9.7 g), m.p. 128°-30° C.

ii) To a stirred suspension of compound I (3.73 g) and zinc chloride (2.5 g) was added ethyl diazoacetate (5 ml). The reaction mixture was heated to 80° C. for 45 minutes (care was taken not to exceed that temperature), cooled and added, dropwise with stirring, to a cooled solution of 1N hydrochloric acid (50 ml). The resultant solution was extracted with chloroform; the chloroform extracts were combined, washed with water, washed with brine, dried and evaporated under reduced pressure to give a semi-solid residue. This was triturated with ether and crystallised from ethyl acetate to give compound II (1.46 g); NMR (CDCl$_3$) 1.49(t,3H); 3.83(s,6H); 4.53 and 4.60(q,2H); 5.56(s,2H); 6.68-6.86(m,3H); 7.20-7.42(m,3H); 7.81 and 7.86(dd,1H); 8.1-8.6(br s,1H); m/e 383.

iii) To a stirred solution of compound II (4.86 g) in dichloromethane (130 ml) at −70° C., in an atmosphere of argon, was added boron tribromide (6.1 ml) in dichloromethane (15 ml). The reaction mixture was allowed to warm to room temperature, stirred overnight and poured on to iced water (600 ml). To this was added potassium hydroxide solution (15 g in 50 ml) to take the pH to 11. The aqueous layer was collected, acidified to pH 1 with concentrated HCl (6 ml) and the precipitate was collected by filtration. This was purified by column chromatography (HP 20 SS column) eluting with aqueous acetonitrile containing 0.1% $CF_3COOH$ to give compound III (1.8 g); NMR (DMSO-$d_6$) 5.44(s,2H); 6.5-6.72(m,3H); 7.17-7.58(m,4H); 8.4-9.2(br s,2H); m/e 284 $(M+H)^+$—$CO_2$.

EXAMPLE 10

7-[2-(2-Aminothiazol-4-yl)-2-((Z)-1-carboxy-1-methylethoxyimino)acetamido]-3-(1-(3,4-dihydroxyphenyl)-5-hydroxy-4-oxopyridine-2-carboxamidomethyl)ceph-3-em-4-carboxylic acid

EXAMPLE 11

7-[2-(2-Aminothiazol-4-yl)-2-((Z)-1-carboxy-1-methylethoxyimino)acetamido]-3-[N-ethyl-N'-(3-bromo-4,5-dihydroxybenzoyl)-L-prolinecarboxamidomethyl]-ceph-3-em-4-carboxylic acid

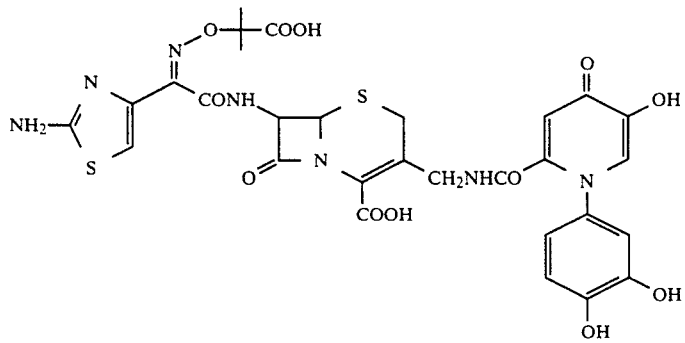

acid (80 mg, 0.3 mM) in dimethylsulphoxide (6 ml) was stirred at room temperature for 90 minutes with dicyclohexylcarbodiimide (63 mg, 0.3 mM) and N-hydroxysuccinimide (35 mg, 0.3 mM). A solution of 3-aminomethyl-7-[2-(2-aminothiazol-4-yl)-2-((Z)-1-carboxy-1-methylethoxyimino)acetamido]ceph-3-em-4-carboxylic acid (145 mg, 0.3 mM) in dimethylsulphoxide (2 ml) containing triethylamine (167 μl, 1.2 mM) was added and the reaction was monitored by HPLC. When all the reactants had been consumed the solvent was removed by evaporation and the residue washed with water, the crude material being collected by filtration. Purification by HPLC on C18 silica (eluting with acetonitrile, water, trifluoroacetic acid, 20:80:0.1) yielded the title compound (60 mg); NMR (D$_6$DMSO, CF$_3$COOH); 1.51(s,3H); 1.53(s,3H); 2.94(d,1H); 3.18(d,1H); 3.85(dd,1H); 4.36(dd,1H); 5.02(d,1H); 5.8(dd,1H); 6.72(dd,1H); 6.80(d,1H); 6.88(d,1H); 7.06(s,1H); 7.29(s,1H); 8.04(s,1H); 9.05(t,1H); 9.54(d,1H).

The starting-material was obtained as follows:

2',2'-Dimethyl-6-amino-1,3-benzodioxal (1.04 g, 6.3 mM) was partially dissolved in water (15 ml) containing concentrated hydrochloric acid (300 μl). 5-0-Benzyl-4-pyrone-2-carboxylic acid (1.23 g, 5 mM) was added and the suspension was refluxed for 6 hours. On cooling a black viscous oil separated which rapidly solidified. This was broken-up, collected by filtration, washed with dichloromethane and dried overnight to yield 1-(3,4-dihydroxyphenyl)-5-0-benzyl-4-oxopyridine-2-carboxylic acid (1.41 g) NMR: (d$_6$DMSO); 5.03(s,2H); 6.52(s,1H); 6.62(dd,1H); 6.72(d,1H); 6.79(d,1H); 7.38(m,5H); 7.55(s,1H).

1-(3,4-Dihydroxyphenyl)-5-0-benzyl-4-oxopyridine-2-carboxylic acid (177 mg, 0.5 mM), suspended in 5 M hydrochloric acid (2 ml) was refluxed for 40 minutes to produce a clear solution. Storage of this overnight at −20° C. yielded 1-(3,4-dihydroxyphenyl-4-hydroxy-4-oxopyridine-2-carboxylic acid as a pale brown crystalline solid (111 mg) NMR (d$_6$DMSO); 6.77(dd,1H); 6.88(d,1H); 7.00(d,1H); 7.52(s,1H); 8.12(s,1H).

7-[2-(2-Aminothiazol-4-yl)-2-((Z)-1-carboxy-1-methylethoxyimino)acetamido]-3-[N-ethyl-N'-tert-butyloxycarbonyl-L-proline carboxamidomethyl]ceph-3-em-4-carboxylic acid (156 mg: 0.22 mmol) was deprotected by stirring at room temperature with trifluoroacetic acid (TFA) (1 ml) for 1 ½ hours. The TFA was removed under reduced pressure and the residue so obtained was freed from residual TFA by evaporating, under reduced pressure, from toluene/DMF. The residue was dissolved in DMF (1 ml) and Et$_3$N was added to the solution until the pH was 7 and then further Et$_3$N (138 μl; 101 mg) was added.

3-Bromo-4,5-discetoxy benzoic acid (70 mg; 0.22 mmol) was converted into 3-bromo-4,5-diacetoxybenzoylchloride by treatment with PCL$_5$ (46 mg, 0.22 mmol) in toluene (1 ml) at 60° C. under argon for 2 hours. The solvent was evaporated and the residue dried under a high vacuum. The dried acid chloride in CH$_2$Cl$_2$ (1 ml) was added dropwise, under an atmosphere of argon, to the solution of the cephalosporin (pre-cooled in an ice-bath). The mixture was stirred at 0° C. for 10 minutes and at room temperature for 1 hour before being stored at −20° C. overnight.

The reaction mixture was concentrated under reduced pressure (to remove CH$_2$Cl$_2$) and the solution diluted with H$_2$O (4 ml) before being treated with (NH$_4$)$_2$CO$_3$ (150 mg). The mixture was stirred at room temperature until HPLC analysis of the reaction mixture indicated that the deprotection reaction was completed. The mixture was acidified with glacial acetic acid (to pH 3) and the title compound isolated by freeze-drying appropriate fractions following chromatography on Dynamax C$_{18}$ reverse phase silica (eluting with a mixture of CH$_3$CN (27.5%), H$_2$O (72.5%) and 0.1% TFA. Mass spectrum —ve FAB (M-H)$^-$824 NMR(d$_6$DMSO/TFA)-the spectrum was run at 60° C. to overcome restricted rotation about tertiary amide bonds: 1.10,(t,3H): 1.53(s,6H): 1.6–2.3 (br,4H); 3–3.6(br,6H); 4.3–4.5(b,3H); 5.16(d,1H); 5.77(m,1H); 6.8–7.1(m,3H).

The starting material was prepared as follows:

3-Ethylaminomethyl-7-[2-(2-aminothiazol-4-yl)-2-((Z)-1-carboxy-1-methylethoxyimino)acetamido]ceph-3-em-4-carboxylic acid (51 mg; 0.1 mmol) and triethylamine (50.5 mg, 69.2 μl) were dissolved in DMSO (0.5 ml) and this solution was treated with 3,4-dihydro-3-hydroxy-4-oxo-1,2,3-benzotriazinyl L-proline (35 mg;

0.1 mmol) dissolved in DMSO (0.5 ml). The mixture was stirred at room temperature for 6 hours (HPLC analysis of an aliquot on reverse phase silica showed that the reaction has gone to completion); diluted with H₂O (5 ml) and acidified with glacial acetic acid. The solution was filtered before being subjected to chromatography on a Dynamax C$_{18}$ reverse phrase silica column. The product was eluted with a mixture of CH$_3$CN (27.5%), H₂O (72.5%) and TFA (0.1%). Appropriate fractions of pure product were combined and freeze-dried. Mass Spec —ve FAB (M-H)⁻708.

3,4-Dihydro-3-hydroxy-4-oxo-1,2,3-benzotriazinyl L-proline was obtained as follows:

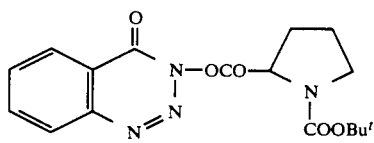

N-t-Butyloxycarbonyl L-proline (1.08 g; 0.5 mmol) and 3,4-dihydro-3-hydroxy-3-oxo-1,2,3-benzotriazine (0.82 g, 0.5 mmol) were suspended in CH$_3$CN (13 ml) and dicyclohexylcarbodiimide (1.1 g; 0.54 mmol) was added. The mixture was stirred at room temperature for 18 hours. The dicyclohexyl urea was removed by filtration and the filtrate evaporated under reduced pressure to give a gum which was purified by chromatography on silica (eluting with 30% EtOAc/70% CH$_2$Cl$_2$) to give the desired compound (1.2 g); NMR (CDCl$_3$) 1.9-2.2(m,2H); 2.4-2.6(m,2H); 3.45-3.75(m,2H); 4.68(m,1H); 7.85(t,1H); 8.01(m,1H); 8.23(d,1H); 8.36(m,1H).

EXAMPLE 12

7-[2-(2-Aminothiazol-4-yl)-2-((Z)-1-carboxy-1-methylethoxyimino)acetamido-3-(1-(3,4-dihydroxyphenyl)-2-methyl-4-oxopyridin-3-carboxamidomethyl)ceph-3-em-4-carboxylic acid

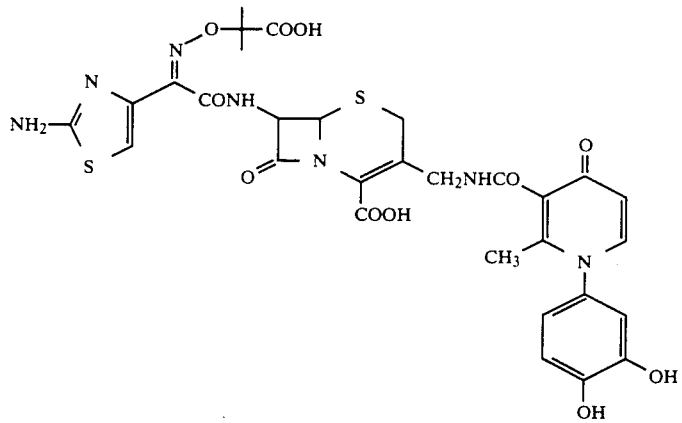

To a suspension of 3-aminomethyl-7-[2-(2-aminothiazol-4-yl)-2-((Z)-1-carboxy-1-methylethoxyimino)acetamido]ceph-3-em-4-carboxylic acid (1 mmole) in CH$_2$Cl$_2$ was added at room temperature Et$_3$N (8 mmoles). The reaction mixture was stirred for 1 hour, then chlorotrimethylsilane was added to the solution and stirring was continued for an additional hour. After cooling in an ice bath, a solution of the acid chloride derivative of compound (4) (obtained by heating acid 4 (1.1 mmoles) with thionyl chloride (10 ml) for 30 seconds and evaporating the excess thionyl chloride) in CH$_2$Cl$_2$ (10 ml) was added. The solution was then acidified with 1N HCl (1 ml) and diluted with water (5 ml). The solution was concentrated, the residue taken up in H$_2$O (20 ml) and the pH adjusted and maintained at 8.0 with 1% NH$_4$OH. After 1 hour at room temperature, the solution was acidified with AcOH and purified on a Diaion HP2OSS resin column (100 ml) using a gradient of MeOH/H$_2$O with 1% AcOH. Fractions containing the desired product were combined, partially evaporated and freeze-dried to give the title compound (211 mg). NMR (DMSOd$_6$+AcOD+TFA): 1.55(br s, 6H); 2.25(s,3H); 3.35-3.90(m,2H); 4.15(d,1H); 4.55(d,1H); 5.16(d,1H); 5.85(d,1H); 6.65-7.15(m,3H); 7.05(s,1H); 7.20(d,1H); 8.43(d,1H).

The starting material was prepared as follows:

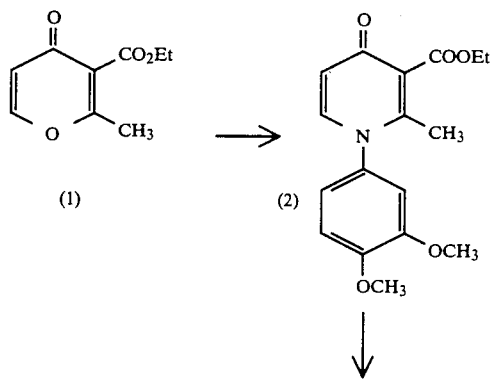

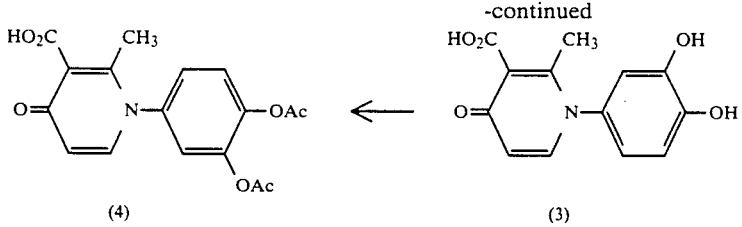

a) To a solution of ethyl 4H-pyran-4-one-2-methyl-3-carboxylate (16 mmoles) (U.S. Pat. No. 4,051,142) in toluene (20 ml) was added aminoveratrol (16 mmoles). The mixture was refluxed for 1 hour. The crystalline product obtained after cooling was collected and dried in vacuo to give compound 2 (650 mg). NMR (CDCl₃);

1.36(t,3H);  2.06(s,3H);  3.90(s,3H);  3.95(s,3H); 4.37(q,2H);  6.36(d,1H);  6.77(s,1H);  6.8–7.0(m,2H); 7.32(d,1H).

b) Compound (2) (1.42 mmoles) and fuming HBr (15 ml) were refluxed for 1.5 hours. After cooling, ice (20 g) was added to the reaction mixture. The crystalline product which deposited was filtered off and washed with isopropanol and ether to give compound (3) (265 mg) NMR (DMSOd₆); 2.58 (s,3H); 6.70(d,1H); 6.7014 6.95(m,3H); 8.02(d,1H).

c) Compound (3) (0.83 mmoles) in acetic anhydride (10 ml) was stirred at 80° C. for 3 hours. After evaporation of the acetic anhydride, the reside was taken up in H₂O (5 ml) and acetone (5 ml) and stirred overnight at room temperature. Acetone was evaporated and a crystalline material deposited. The solid was filtered off, washed successively with isopropanol and ether and dried to give compound (4) (235 mg) NMR (DMSOd₆+TFA); 2.27(s,3H); 2.30(s,3H); 2.48(s,3H); 6.80(d,1H); 7.40–7.65(m,3H); 8.25(d,1H).

EXAMPLE 12

7-[2-(2-Aminothiazol-4-yl)-2-((Z)-1-carboxy-1-methylethoxyimino)acetamido-3-(1-(3,4-dihydroxyphenyl)-2-oxo-tetrahydroimidazolin-3-carboxamidomethyl)ceph-3-em-4-carboxylic acid

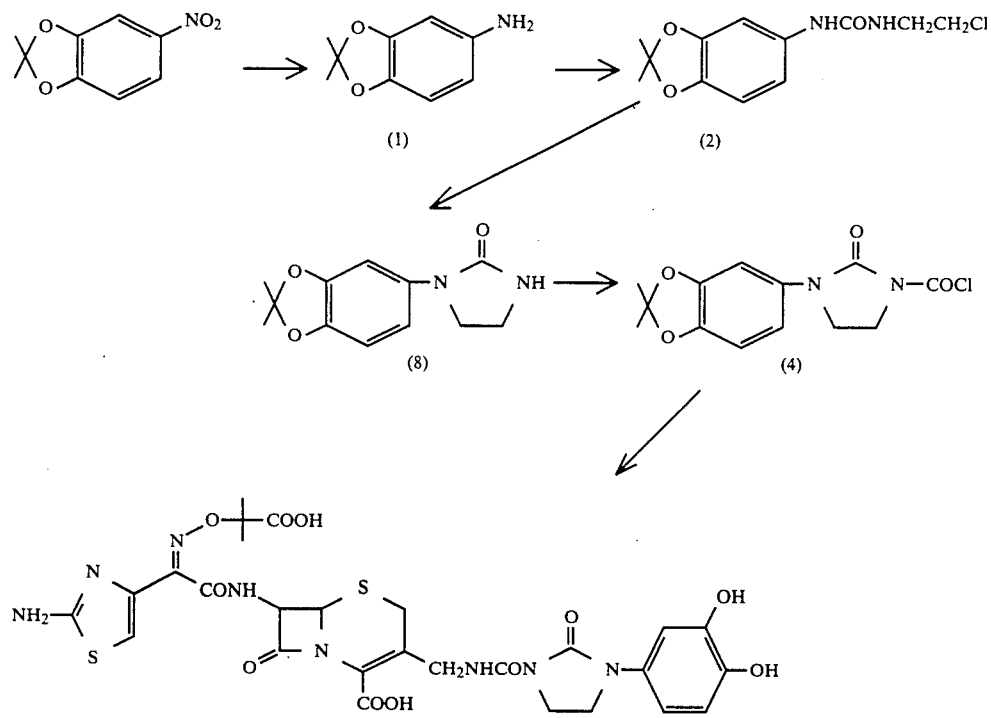

3-Aminomethyl-7-[2-(2-aminothiazol-4-yl)-2-((Z)-1-carboxy-1-methylethoxyimino)acetamido]ceph-3-em-4-carboxylic acid (0.31 mmoles) was dissolved in DMSO (10 ml) and Et₃N (1.43 mmoles) added, followed by compound (4) (0.2 mmoles). The mixture was stirred at room temperature for 0.5 hours. The crude reaction mixture was purified using HP2OSS resin (120 ml) chromatography eluting with H₂O/MeOH mixture of increasing proportions of MeOH and containing AcOH (1%). The cephalosporin thus isolated was dissolved in CH₂Cl₂ (1 ml). The TFA (1 ml) was added to the mixture and this was stirred at room temperature for 1 hour. The solvents were evaporated and the residue chromatographed over HP2OSS resin (120 ml) using a gradient of MeOH/H₂O with 1% AcOH. Fractions containing the desired product were combined and evaporated, the residue taken up in the minimum volume of MeOH and further precipitated with ether to give the title compound (22 mg). NMR (DMSOd₆.+AcOD+TFA); 1.54 (br s,6H); 3.4–4.5(m,8H); 5.2(d,1H); 5.94(d,1H); 6.70(br s,2H); 7.0–7.25(m,2H).

The starting-material was prepared as follows:

a) The nitroacetamide (10 mmoles) (Aust. J. Chem 33 p. 675, 1980) dissolved in EtOH (75 ml) and 5% palladium on charcoal (200 mg) were stirred under an atmosphere of hydrogen (1.5 hr). After 2 hours, the mixture was filtered through diatomaceous earth and washed with EtOH. The solvent was evaporated to give the aminoacetamide (1) (1.62 g) NMR (CDCl$_3$); 1.63(s,6H); 3.30(br s,2H); 6.07(dd,1H); 6.20(d,1H); 6.52(d,1H).

b) To compound (1) (2.8 mmoles) dissolved in anhydrous CH$_2$Cl$_2$ (20 ml) was added dropwise 2-chloroethylisocyanate (10.8 mmoles). AFter stirring at room temperature for 1.5 hours, the reaction mixture was partially concentrated and ether was added to the residue. The precipitate was collected to give compound (2) (2.44 g) NMR (CDCl$_3$); 1.62(s,6H); 3.54(br s,4H); 5.4(br s,1H); 6.5–6.8(m,4H).

c) Compound (2) (5 mmoles) was added to a solution of KOH (10 mmoles) in EtOH (6 ml) and H$_2$O (2ml). The mixture was refluxed for 10 minutes and diluted with water. The precipitated crystals were collected by filtration to give compound (3) (0.98 g) NMR (CDCl$_3$); 1.65(s,6H); 3.6–4.0(m,4H); 4.95(br s,1H); 6.67(d,2H); 7.16(s,1H).

d) To compound (3) (0.5 mmoles) in CHCL$_3$ was added to 20% solution of phosgene in toluene (1 ml). The reaction mixture was refluxed for 1.5 hours; additional phosgene (1 ml) was added and the reflux continued for another 1.5 hours. After cooling, the solvent was evaporated under vacuum to yield compound (4) (124 mg) NMR (DMSOd$_6$); 1.63(s,6H); 3.3–4.0(m,4H); 6.73(s,2H); 7.26(s,1H).

We claim:

1. A compound of the formula (V):

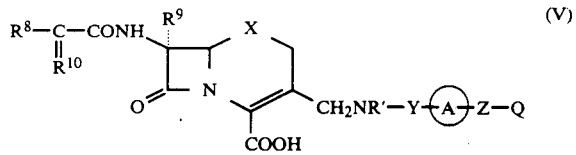

wherein

Q is phenyl or naphthyl substituted by groups $R^2$ and $R^3$ which are ortho with respect to one another and wherein $R^2$ is hydroxy or an in vivo hydrolysable ester group thereof and $R^3$ is hydroxy or an in vivo hydrolysable ester group thereof, Q being optionally substituted by C$_{1-6}$ alkyl, halo, hydroxy, hydroxy C$_{1-6}$ alkyl, cyano, trifluoromethyl, nitro, amino, C$_{16}$ alkylamino, di-C$_{1-6}$ alkylamino, amino C$_{1-6}$ alkyl, C$_{1-6}$ alkylamino C$_{1-6}$ alkyl, di-C$_{1-6}$ alkylamino C$_{1-6}$ alkyl, C$_{1-6}$ alkanoyl, C$_{1-6}$ alkoxy, C$_{1-6}$ alkylthio, C$_{1-6}$ alkanoyloxy, carbamoyl, C$_{1-6}$ alkylcarbamoyl, di-C$_{1-6}$ alkyl carbamoyl, carboxy, carboxy C$_{1-6}$ alkyl, sulpho, sulpho C$_{1-6}$ alkyl, C$_{1-6}$ alkanesulphonamido, C$_{1-6}$ alkoxycarbonyl, C$_{1-6}$ alkanoylamino, nitroso, thioureido, amidino, ammonium, mono-, di- or tri-C$_{1-6}$ alkylammonium or pyridinium, or a 5-membered heterocyclic ring consisting of 1 to 4 hetero ring atoms selected from oxygen, nitrogen and sulphur, the remaining ring atoms being carbon and said ring being optionally substituted by 1, 2 or 3 C$_{1-6}$ alkyl or C$_{1-6}$ alkoxy groups;

$R^1$ is hydrogen, C$_{1-6}$ alkyl optionally substituted by any of halo, hydroxy, C$_{1-6}$ alkoxy, carboxy, amino, cyano, C$_{1-6}$ alkanoylamino, phenyl or heteroaryl, or $R^1$ is C$_{2-6}$ alkenyl;

Y is —CO— or —SO$_2$—;

X is sulphur or sulphinyl;

Z is a direct bond, C$_{1-4}$ alkylene, C$_{2-4}$ alkenylene, C$_{2-4}$ alkynylene, —CO—, —(CH$_2$)$_n$NR$^4$CO— or —CONR$^4$(CH$_2$)$_n$— wherein n is 0 to 4;

$R^4$ is hydrogen or C$_{1-6}$ alkyl; $R^9$ is hydrogen, methoxy or formamido;

$R^8$ is 2-aminothiazol-4-yl or 2-aminooxazol-4-yl each optionally substituted in the 5-position by fluorine, chlorine or bromine, or $R^8$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-thiazol-3-yl;

$R^{10}$ is of the formula —N.O.R$^{11}$ (having the syn configuration about the double bond) wherein $R^{11}$ is hydrogen, (1–6C)alkyl, (3–8C)cycloalkyl, (1–3C)alkyl(3–6C)cycloalkyl, (3–6 C) cycloalkyl (1–3-C)alkyl, (3–6C)alkenyl, optionally substituted by carboxy, (5–8C)cycloalkenyl, (3–6C) alkynyl, (2–5C) alkylcarbamoyl, phenylcarbamoyl, benzylcarbamoyl, (1–4C)alkylcarbamoyl(1–4C)alkyl, di(-1–4C) alkylcarbamoyl(1–4C)alkyl, (1–4C)haloalkylcarbamoyl(1–4C)alkyl, (1–3C)haloalkyl, (2–6C)hydroxyalkyl, (1–4C)alkoxy(2–4C)alkyl, (1–4C)alkylthio(2–4C)alkyl, (1–4C)alkanesulphinyl(1–4C)alkyl, (1–4C)alkanesulphonyl(1–4C)alkyl, (2–6C)aminoalkyl, (1–4C)alkylamino(1–6C)alkyl, (2–8C)dialkylamino(2–6C)alkyl, (1–5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or $R^{11}$ is of the formula (VI):

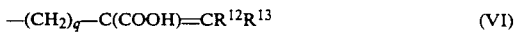

wherein q is one or two and $R^{12}$ and $R^{13}$ are independently hydrogen or C$_{1-4}$alkyl; or $R^{11}$ is of the formula (VII):

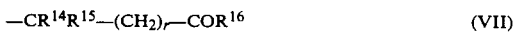

wherein r is 0–3, $R^{14}$ is hydrogen, (1–3C)alkyl or methylthio, $R^{15}$ is hydrogen (1–3C)alkyl, (3–7C)cycloalkyl, cyano, carboxy, (2–5C)carboxylalkyl or methanesulphonylamino, or $R^{14}$ and $R^{15}$ are joined to form, together with the carbon to which they are attached, a (3–7C)carbocyclic ring, and $R^{16}$ is hydroxy, amino, (1–4C)alkoxy, (1–4C)alkylamino or of the formula NHOR$^{17}$ in which $R^{17}$ is hydrogen or (1–4C)alkyl;

or $R^{10}$ may be of the formula —CH.4$^{18}$ wherein $R^{18}$ is hydrogen, halogen, (1–6C)alkyl, (3–7C)cycloalkyl, (2–6C)alkenyl, (3–7C)cycloalkenyl phenyl or benzyl; and A is a phenylene ring or a 5- or 6-membered heterocyclic ring consisting of 1, 2, or 3 ring atoms selected from nitrogen, oxygen and sulphur with the remaining ring atoms being carbon atoms, either ring being unsubstituted or substituted by C$_{1-6}$ alkyl, halo, hydroxy, hydroxy C$_{1-6}$alkyl, cyano, trifluoromethyl, nitro, amino, C$_{1-6}$alkylamino, di-C$_{1-6}$-alkylamino, C$_{1-6}$alkanoyl, C$_{1-6}$alkoxy, C$_{1-6}$alkylthio, C$_{1-6}$alkanoyloxy, carbamoyl, C$_{1-6}$alkylcarbamoyl, di-C$_{1-6}$alkyl carbamoyl, carboxy, carboxy $C_{1-6}$alkyl, $C_{1-6}$alkoxycarbonyl$C_{1-6}$alkyl, sulpho, sulpho$C_{1-6}$alkyl, sulphonamido $C_{1-6}$alkyl, $C_{1-6}$alkoxycarbonyl, $C_{1-6}$alkanoylamino, thioureido or amidino, and the ring A being unfused or fused to a benzene ring.

2. A compound according to claim 1 wherein $R^2$ and $R^3$ are both hydroxy.

3. A compound according to claim 1 wherein the compound has a 3-position substituent which is: 2-(3,4-dihydroxyphenyl)-pyridin-5-carboxamidomethyl, 2-(2-bromo-4,5-dihydroxyphenyl)pyridin-5-carboxamidomethyl, 4-(3,4-dihydroxyphenyl)pyridin-3-carboxamidomethyl, 2-(3,4-dihydroxyphenyl)-4-oxopyrimidin-5-carboxamidomethyl or 2-(3,4-diacetoxyphenylcarbamoyl)pyridin-5-carboxamidomethyl.

4. A compound according to claim 1 wherein $R^{11}$ is 2-carboxyprop-2-yl.

5. A compound which is:
- 7-[2-(2-Aminothiazol-4-yl)-2-((Z)-1-carboxy-1-methylethoxyimino)acetamido]-3-(2-(3,4-dihydroxyphenyl)pyridin-5-carboxamidomethyl)ceph-3-em-4-carboxylic acid,
- 7-[2-(2-Aminothiazol-4yl)-2-((Z)-1-carboxy-1-methylethoxyimino)acetamido]-3-[2-(3,4-dihydroxyphenyl)-4-oxopyrimidin-5-carboxamidomethyl]ceph-3-em-4-carboxylic acid,
- 7-[2-(2-Aminothiazol-4-yl)-2-((Z)-1-carboxy-1-methylethoxyimino)acetamido]-3-(2-(3,4-diacetoxyphenylcarbamoyl)pyridin-5-carboxamidomethyl)ceph-3-em-4-carboxylic acid,
- 7-[2-(2-Aminothiazol-4-yl)-2-((Z)-1-carboxy-1-methylethoxyimino)acetamido]-3-(2-(3,4-dihydroxybenzoyl)pyridin-3-carboxamidomethyl)ceph-3-em-4-carboxylic acid,
- 7-[2-(2-Aminothiazol-4-yl)-2-((Z)-1-carboxy-1-methylethoxyimino)acetamido]-3-(3-(3,4-dihydroxybenzoyl)pyridin-2-carboxamidomethyl)ceph-3-em-4-carboxylic acid,
- 7-[2-(2-aminothiazol-4-yl)-2-((Z)-1-methoxyethoxyimino)acetamido]-3-(1,2-dihydro-1-(3,4-dihydroxybenzyl)-3-hydroxy-2-oxoquinolin-4-carboxamidomethyl)ceph-3-em-4-carboxylic acid,
- 7-[2-(2-aminothiazol-4-yl)-2-((Z)-1-carboxy-1-methoxyethoxyimino)acetamido]-3-(1-(3,4-dihydroxyphenyl)-5-hydroxy-4-oxopyridine-2-carboxamidomethyl)ceph-3-em-4-carboxylic acid,
- 7-[2-(2-Aminothiazol-4-yl)-2-((Z)-1-carboxy-1-methylethoxyimino)acetamido]-3-[N-ethyl-N'-(3-bromo-4,5-dihydroxybenzoyl)-L-prolinecarboxamidomethyl]ceph-3-em-4-carboxylic acid,
- 7-[2-(2-aminothiazol-4-yl)-2-((Z)-1-carboxy-1-methylethoxyimino)acetamido]-3-(1-(3,4-dihydroxyphenyl)-2-methyl-4-oxopyridin-3-carboxamidomethyl)ceph-3-em-4-carboxylic acid, or
- 7-[2-(2-aminothiazol-4-yl)-2-((Z)-1-carboxy-1-methylethoxyimino)acetamido]-3-(1-(3,4-dihydroxyphenyl)-2-oxotetrahydroimidazolin-3-carboxamidomethyl)ceph-3-em-4-carboxylic acid.

6. A pharmaceutical composition which comprises a compound according to claim 1 and a pharmaceutically acceptable carrier.

* * * * *